United States Patent [19]

Kira et al.

[11] Patent Number: 4,720,842
[45] Date of Patent: Jan. 19, 1988

[54] APPARATUS FOR DETECTING NICKEL/VANADIUM CONTAINED IN OIL

[75] Inventors: Akimichi Kira; Yoshinori Hosokawa, both of Kyoto, Japan

[73] Assignee: Horiba, Ltd., Kyoto, Japan

[21] Appl. No.: 844,018

[22] Filed: Mar. 25, 1986

[30] Foreign Application Priority Data

Jun. 8, 1985 [JP]  Japan ............... 60-124597

[51] Int. Cl.$^4$ ............................................. G01N 23/223
[52] U.S. Cl. ............................................. 378/49; 378/45; 378/47
[58] Field of Search ..................... 378/45, 47, 49, 83

[56] References Cited

U.S. PATENT DOCUMENTS 3,919,548  11/1975  Porter ................................. 378/45
4,349,738  9/1982  Baecklund .......................... 378/49

Primary Examiner—Janice A. Howell
Assistant Examiner—David P. Port
Attorney, Agent, or Firm—Wenderoth, Lind & Ponack

[57] ABSTRACT

An apparatus for detecting heavy metals in an oil sample which radiates X-rays from a target type X-ray tube through an iron filter and then upon a sample cell containing the oil to be measured therein and detects fluorescent X-rays excited in the oil by an energy dispersion type fluorescent X-ray detector.

5 Claims, 2 Drawing Figures

APPARATUS FOR DETECTING NICKEL/VANADIUM CONTAINED IN OIL

BACKGROUND OF THE INVENTION

1. Field of the Invention

The present invention relates to an apparatus for detecting nickel/vanadium contained in an oil. The present invention is useful in conjunction with evaluating oil to determine the existence, concentration and the like of nickel (Ni) and vanadium (V), which are heavy metals contained in oils such as crude oil and heavy oil.

2. Description of the Prior Art

Apparatus for detecting nickel/vanadium contained in an oil utilizing an atomic absorption method and a wave-length dispersion type X-ray fluorescence method have been known.

However, the former method, which utilizes an atomic absorption method, has a disadvantage in that a remarkably troublesome and time consuming pretreatment of the oil to be measured is necessary. This treatment involves heating the oil to be measured together with concentrated sulfuric acid until it is carbonized and then heat treating the resultant product at 575° C. under a dry atmosphere to turn it into an ash which is subsequently dissolved in a reagent. That is to say, for example, if the quantity of oil to be treated is 20 g, it takes 20 hours for heating/carbonizing and one night for turning the resultant product into an ash under a dry atmosphere. Also, in the heating/carbonizing operation, a subtle control of the heating temperature and agitation of the mixture are always required in order to prevent an abrupt boiling of the mixture from occurring.

Also, the latter method, which utilizes a wave-length dispersion type X-ray fluorescence method, has a disadvantage in that it is necessary to sufficiently increase the distance of an X-ray fluorescence-measuring path from a sample cell, in which the oil to be measured is housed, to a wave-length dispersion type X-ray fluorescence detector. As a result, the measuring path must be adapted to be maintained under a vacuum atmosphere so that fluorescent X-rays may not be absorbed and attenuated in the long measuring path and consequently, steps must be taken to prevent the dispersion due to boiling of the oil sample in a vacuum atmosphere. Such steps necessitate a remarkably troublesome and time consuming pretreatment of the oil to be measured, such as a treatment for turning the oil into an ash sample as well as melting and glassification of each sample. The pretreatment steps are similar to those used in the apparatus utilizing an atomic absorption method and the apparatus as a whole is large-sized and complicated.

SUMMARY OF THE INVENTION

The present invention overcomes the disadvantages of the above described prior art devices by providing an apparatus for detecting nickel/vanadium contained in an oil in which the requirement for a remarkably troublesome and time consuming pretreatment operation of an oil sample can be eliminated. The apparatus of the present invention is relatively small-sized and simple, and the detection method according to the present invention can be carried out with high accuracy.

In order to achieve the above described object, an apparatus for detecting nickel/vanadium contained in an oil according to the present invention is characterized in that a target type X-ray tube radiates X-rays through an iron (Fe) filter and upon a sample cell containing oil to be measured therein and an energy dispersion type X-ray fluorescence detector receives fluorescent X-rays excited by the oil contained in said sample cell.

The effects due to such a characteristic construction are as follows:

First, since the apparatus according to the present invention utilizes an energy dispersion type X-ray fluorescence analysis in which fluorescent X-rays are excited by X-rays radiated upon an oil to be measured contained in a sample cell, it is not necessary to increase a fluorescent X-ray measuring path and utilize a construction, in which the measuring path is maintained under a vacuum condition as in the conventional apparatus utilizing a wave-length dispersion type X-ray fluorescence analysis. As such, the requirement for a remarkably troublesome and time consuming pretreatment operation of the oil to be measured, such as a treatment for heating and carbonizing the oil to be measured, a treatment for turning the oil to be measured into an ash or the melting and glassification of the sample can be eliminated. Instead, according to the present invention, the oil to be measured can be used for a sample as is in an air atmosphere and the apparatus as a whole can be small-sized and simple in construction.

In addition, since X-rays radiated from a target type X-ray tube are not directly incident upon said sample cell as they are but rather, they are incident upon said sample cell after passing through an iron (Fe) filter, two kinds of heavy metals, such as nickel (Ni) and vanadium (V), can be surely and accurately detected by one detecting operation.

That is to say, it has been found during the development process of said apparatus according to the present invention that when an apparatus is used utilizing the energy dispersion type X-ray fluorescence analysis, a basic problem occurs in that scattered X-rays resulting from light metals, which are main ingredients of an oil to be measured, enter an energy dispersion type fluorescent X-ray detector and become a background for the measured characteristic X-rays of two kinds of heavy metals, such as nickel (Ni) and vanadium (V) resulting in lowering of the measuring accuracy for these metals. A contradictory problem occurs in that if a condition optimum for the measurement of characteristic X-rays of nickel (Ni-K$\alpha$) is selected by the use of a filter, the measured strength of characteristic X-rays of vanadium (V-K$\alpha$) is reduced (an output for use in measurement is reduced) while if a condition optimum for the measurement of characteristic X-rays of vanadium (V-K$\alpha$) is selected, a background of characteristic X-rays of nickel (Ni-K$\alpha$) is heightened (an influence of interference components is increased and as a result, an output for use in measurement is reduced).

According to the present invention, it has been found that X-rays radiated from a target type X-ray tube passed through an iron (Fe) filter reduces a background of characteristic X-rays of nickel (Ni-K$\alpha$) and the charateristic X-rays of vanadium (V-K$\alpha$) are sufficiently excited by continuous X-rays between the characteristic X-rays of nickel (Ni-K$\alpha$) and the characteristic X-rays of vanadium (V-K$\alpha$). This phenomenon was discovered only after repeated experimental studies using various kinds of filters and thus, the apparatus of the present invention utilizes an iron (Fe) filter disposed between the target type X-ray tube and the sample cell in order to utilize such a phenomenon.

BRIEF DESCRIPTION OF THE DRAWINGS

The drawings illustrate a preferred embodiment of an apparatus for detecting nickel/vanadium contained in an oil according to the present invention, in which.

DESCRIPTION OF THE PREFERRED EMBODIMENT

The preferred embodiment of the present invention will be described below with reference to the drawings.

Figure 1:
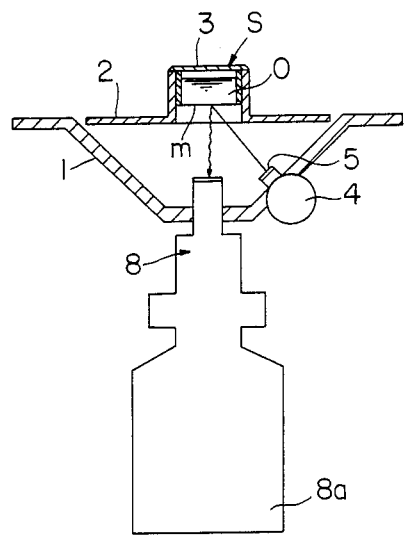
FIG. 1 is a general block diagram.

Referring now to FIG. 1, which is a general block diagram showing an apparatus for detecting a concentration of nickel (Ni) and vanadium (V) contained in crude oil and heavy oil, 1 designates a support means comprising an exciting bench formed of metals and provided with a sample table 2. A plurality of sample cells S containing an oil 0 to be measured therein are exchangeably set in the sample table 2 which is adapted so as to be driven to move each of said cells S sequentially to a designated measuring position. Each sample cell S comprises a cell frame body having an upper cover 3 and a mylar film m adhered to a bottom thereof and the sample cell S is adapted to contain the oil 0 to be measured therein.

The exciting bench 1 is provided with a tungsten (W) target type X-ray tube 4 for radiating X-rays to a sample cell S positioned at the designated measuring position on the sample table 2 such that the X-rays are incident upon the oil sample through the mylar film m. An iron (Fe) filter 5 is disposed over an X-ray radiating port of said X-ray tube 4. In short, primary X-rays radiated from the X-ray tube 4 pass through the iron (Fe) filter 5 to become secondary X-rays and are radiated to the oil 0 to be measured which is contained in sample cell S positioned at the designated measuring position.

In addition, said exciting bench 1 is provided with an energy dispersion type fluorescent X-ray detector 8 for detecting fluorescent X-rays which are excited as a result of the oil 0 receiving the secondary X-rays radiated through said iron (Fe) filter 5. This fluorescent X-ray detector 8 is provided with an included preamplifier (not shown) and a cooling dewer 8a.

Figure 2:
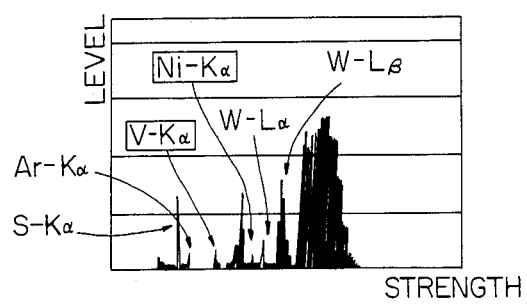
FIG. 2 is a graph showing an energy spectrum as one example of the detected result.

FIG. 2 is a graph showing one example of an energy spectrum taken by an apparatus according to the present invention for detecting nickel/vanadium contained in an oil and which is constructed in the above described manner. As shown in the graph of FIG. 2, the apparatus according to the present invention provides detection of both characteristic X-rays of nickel (Ni-$K\alpha$) and those of vanadium (V-$K\alpha$) while maintaining a small background.

It should be evident that the apparatus for detecting nickel/vanadium contained in an oil according to the present invention eliminates the remarkably troublesome and time consuming prior art pretreatment of oil to be measured involving heating and carbonizing the oil, converting the oil into an ash and melting and glassifying a sample such as is used in the conventional apparatus utilizing an atomic absorption method and a wave-length dispersion type X-ray fluorescence analysis. Instead, the present invention utilizes an energy dispersion type X-ray fluorescence analysis in which X-rays radiated from a target type X-ray tube are incident upon a sample cell after passing though an iron (Fe) filter. Thus, two kinds of heavy metals, such as nickel (Ni) and vanadium (V), can be very efficiently, surely and accurately detected by one quick measuring operation. Furthermore, since the fluorescent X-ray-measuring path is not increased in length and the measuring path is not required to be maintained under a vacuum atmosphere, in contradistinction to the conventional apparatus utilizing a wave-length dispersion type X-ray fluorescence analysis, the apparatus of the present invention as a whole can be remarkably small-sized and simple in construction.

While the invention has been described with reference to the foregoing embodiment, it will be apparent to those skilled in the art that various changes and modifications may be made thereto without departing from the scope of the appended claims.

What is claimed is:

1. An apparatus for detecting nickel and vanadium contained in an oil sample, comprising a sample cell containing an oil sample, a target type X-ray tube having an iron (Fe) filter through which X-rays must pass before hitting said sample cell containing the oil sample and an energy dispersion type fluorescent X-ray detector for detecting fluorescent X-rays excited in the oil sample as a result of the oil sample contained in said sample cell receiving the radiated X-rays which have passed from said X-ray tube and through said iron filter.

2. An apparatus for detecting nickel and vanadium contained in an oil sample, comprising:

a support means;

a sample table disposed on said support means;

at least one sample cell means disposed on said sample table for containing an oil sample in which the presence of nickel and vanadium is to be detected;

a target type X-ray tube means disposed on said support means for radiating X-rays into said oil sample contained in said sample cell means;

an energy dispersion type fluorescent X-ray detector means disposed on said support means for detecting fluorescent X-rays excited in said oil sample; and an iron filter means disposed between said X-ray tube means and said sample cell means for converting primary X-rays from said X-ray tube means into secondary X-rays which pass into said oil sample.

3. The apparatus of claim 2, wherein said at least one sample cell means comprises a plurality of sample cell means, each of which is disposed on said sample table and is movable sequentially into a position at which said X-ray tube means radiates X-rays into an oil sample contained therein.

4. The apparatus of claim 2, wherein said sample cell means comprises a cell frame body having a mylar film adhered to a bottom thereof, said cell frame being disposed with said mylar film oriented towards said X-ray tube means for passage of X-rays through said mylar film and into said oil sample contained in said sample cell means.

5. The apparatus of claim 2, wherein a space between said X-ray tube means, said sample cell means and said fluorescent X-ray detector means comprises an air atmosphere.

* * * * *